US006465396B1

(12) United States Patent
Kobayashi et al.

(10) Patent No.: US 6,465,396 B1
(45) Date of Patent: Oct. 15, 2002

(54) METHOD TO PROMOTE GROWTH OF A PLANT

(75) Inventors: Akio Kobayashi, Toyonaka; Eiichiro Fukusaki, Suita; Akira Isogai, Ikoma, all of (JP)

(73) Assignee: Nara Institute of Science and Technology, Ikoma (JP)

( * ) Notice: Subject to any disclaimer, the term of this patent is extended or adjusted under 35 U.S.C. 154(b) by 0 days.

(21) Appl. No.: 09/517,427

(22) Filed: Mar. 2, 2000

(30) Foreign Application Priority Data

Mar. 4, 1999 (JP) .......................................... 11-056776

(51) Int. Cl.[7] .............................................. A01N 31/00
(52) U.S. Cl. ........................................................ 504/353
(58) Field of Search ............................................ 504/353

(56) References Cited

U.S. PATENT DOCUMENTS 5,597,400 A * 1/1997 Nonomura et al. ............ 71/28

FOREIGN PATENT DOCUMENTS

JP 05112731 * 5/1993

* cited by examiner

*Primary Examiner*—Alton N Pryor
(74) *Attorney, Agent, or Firm*—Burns Doane Swecker & Mathis LLP

(57) ABSTRACT

A concise method to promote growth of a plant useful for increase of food production. This invention provides a method to promote growth of a plant by administration of formic acid, an organic acid with a low molecular weight through avoidance of photo-oxidation damage. This invention also provides amino acid sequence of formate dehydrogenase and base sequence encoding the enzyme. The expression of the enzyme is induced by administration of formic acid and the enzyme is involved in metabolism of formic acid and its salts. Furthermore, this invention provides a method to promote growth of a plant by administration of methanol through avoidance of photo-oxidation damage.

2 Claims, 19 Drawing Sheets

FIG. 13

```
O. sativa       1   ---MAMWRAAAHLLCEALGSRAAHTSAGSKKIVGVFYKGGEYADKNPNFVGCVEGALGI        57
H. vulgare      1   ---MAAMWRAAAAOLLDRAVGSRAAHTSAGSKKIVGVFYQAGEYADKNPNFVGCVEGALGI       58
S. tuberosum    1   MSRVASTAARAITSPSSLVFTREMQASFGPKKIVGVFYKANEVAEMNPFLEAENALGI         60

O. sativa      58   REWLESKGHHYIVTDDKHGLNSELEKHIEDMHVLITTPFHPAYYSAERIKKAKNLELLLT       117
H. vulgare     59   EDMLESKGHHYIVTDDKEFNSELEKHIEDMHVLITTPFHPAYVIAEKIKKAKTPELLLT       118
S. tuberosum   61   REWLESKGHQYIMPDKEGEHDCELEKHIEDLHVLISTPFHPAYTAERIKKANLQLLLT       120

O. sativa     118   AGIGSDHIDLPAAAAAGLTVAEVTGSNTVSVAEDELMRILILLRNFLPGYDVVHGEWNV       177
H. vulgare    119   AGIGSDPHIPLPAAAAAGLTVARVTGSNTVSVAEDELMRILILLRNFLPGYDVVKGEWNV       178
S. tuberosum  121   AGIGSDHVDIKAAAAAGITVAEVTGSNTVSVAEDELMRILIVRNFLPGHHQVINGEWNV       180

O. sativa     178   AGLYRAYDLEKIVCEVGACRYGRLIONKREWCKLANINDPELEKEIEAKYEE          237
H. vulgare    179   AGIAHRAYDLEKTVGTVGIGAVGPLIYQRAFNCNLYNQKIONNPELEKEIGAKFEE         238
S. tuberosum  181   AIAHRAYDLEKIVGAVAGRAGNLYQGVHLINNGELENOIGAKFEE                    240

O. sativa     238   DLDAMI.PKCDVIVINTPLTEKTRGMFNKERIAKMKKGVIIVNNARGAIMXTQAVADACSS    297
H. vulgare    239   DLDAM.PKCDVVVINTPLTEKTRGMFLEKIAKMKKGVIIVNNERSAIMDTQAVADACSS     298
S. tuberosum  241   DIDKVLSKFDIVVINTPLTEKTKGENEDKERFAKLKKGVLIVNNERSAIMDFDAVMIACNS    300

O. sativa     298   GVAGYGGDVWFPQPAPKGPPWRYMPNHAMTPHISGTTIDAQLRYAAGVKDMLDRYFKGE      357
H. vulgare    299   GHIAGYGGDVWFPQPAPKDHPWRYMPNHAMTPHISGTTIDAQLRYAAGVKDMLDRYFKGE     358
S. tuberosum  301   GHIAGVSGDWPOPAPKDHPWRYMPNOAMTPHISGTTIDAQLRYAAGTKDMLDRYFKGE      360

O. sativa     358   DFPVQNYIVKEGQLASQYQ*                                               377
H. vulgare    359   EFPVENYIVKEGELASQYK**                                              379
S. tuberosum  361   DFRAENYIVKDGEHAP                                                   376
```

O. sativa
H. vulgare
S. tuberosum

A: aerial part
R: root

METHOD TO PROMOTE GROWTH OF A PLANT

BACKGROUND OF THE INVENTION

1. Field of the Invention

This invention relates to a method to promote growth of a plant by administration of an organic acid with a low molecular weight to avoid photo-oxidation damage of the plant. This invention also relates to a method to promote growth of a plant by administration of an alcohol to avoid photo-oxidation damage of the plant.

2. Description of Related Art

Nowadays, shortage of food production have became a serious problem because of population explosion throughout the world. Growth and metabolism of a plant are affected by various conditions of surroundings. Photo-oxidation damage is caused by alteration of surrounding conditions and triggered by decrease of carbon dioxide uptake, through closure of stoma under condition of strong light-intensity and droughtiness. Because of shortage of carbon dioxide under such condition, excess amount of energy is acquired by photosynthesis system. As the result, excess amount of active oxygen beyond defense ability of the plant is generated, which results in occurrence of the photo-oxidation damage. As such photo-oxidation damage inhibits plant growth, a method to prevent this phenomenon is desired. Heretofore, a transgenic plant having ability to delete active oxygen have been used for such purpose.

SUMMARY OF THE INVENTION

Despite of it, production of a transgenic plant with such characteristic takes much time and the range of plants suitable for producing such transgenic plant is limited. Therefore, the development of a method to prevent photo-oxidation damage with simplicity and wide-utility have been desired to promote growth of a plant.

It is known that, a plant metabolizes methanol and converts it to carbon dioxide, through formaldehyde and formic acid as the intermediate. Then the inventors administrated formic acid, an organic acid with a low molecular weight, to rice, tabacco and kidney bean and found avoidance of photo-oxidation damage. Moreover, the inventors have investigated effect of formic acid on growth of rice plant bodies and found its effectiveness on growth promotion. Moreover, the induction of formate dehydrogenase (FDH) activity, which metabolizes formic acid to produce carbon dioxide, was observed by administration of formic acid. Furthermore, the amino acid sequence of formate dehydrogenase (FDH) and the base sequence encoding the enzyme were determined. The photo-oxidation damage might be prevented by incorporation of FDH gene.

The inventors have also administrated methanol, an alcohol with a low molecular weight, to avoid photo-oxidation damage of rice, tabacco and kidney bean. Therefore, methanol might be effective for promotion of plant growth.

These and other features and advantages of this invention will become apparent upon a reading of the detailed description and drawings.

BRIEF DESCRIPTION OF THE DRAWINGS

FIG. 13 is a graph showing amino acid sequence of rice formate dehydrogenase, compared with that of potato formate dehydrogenase and barley formate dehydrogenase.

Figure 1:
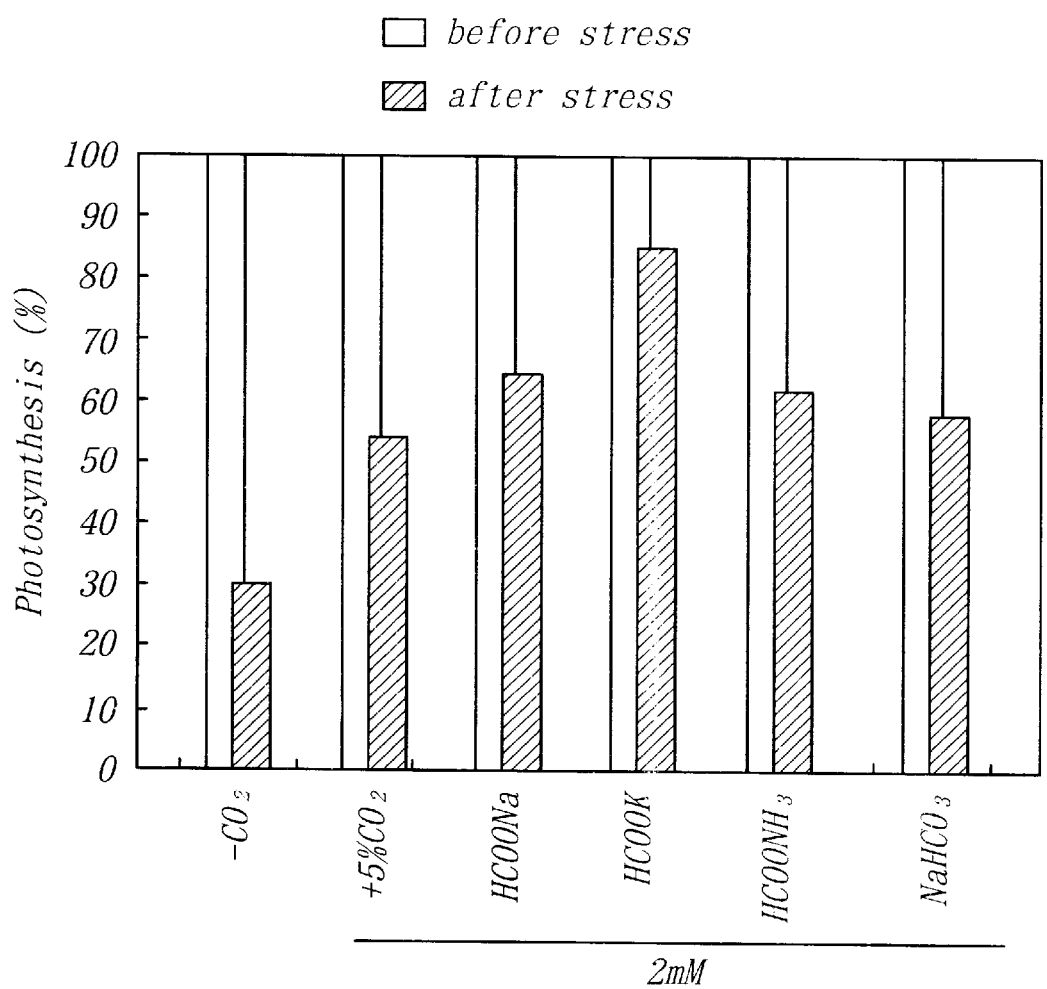
FIG. 1 is a graph showing effects of various formate salts on photo-oxidation damage of rice.

DETAILED DESCRIPTION OF EMBODIMENTS (The Plant Bodies Utilized for the Experiments)

(1) Rice

The seeds of rice (*Oryza sativa* L.: Hinihikari) were used for the experiments. The plants were seeded under a vermiculight. They were grown under a light intensity of 150 $\mu$mol quanta/m$^2$.s for 16 hours in the light and 8 hours in the dark. Normal leaves derived from the plant bodies of 2 to 4 weeks old were used for the following experiments.

(2) Tabacco

The seeds of tabacco (*Nicotina tabacum* L.: SRI) were used for the experiment. The plants were seeded under a vermiculight. They were grown under the light intensity of 150 $\mu$mol quanta/m$^2$·s. Normal leaves derived from the plant bodies of 4 to 6 weeks old were used for the experiments.

(3) Kidney Bean

The seeds of kidney bean (*Phaseolus vulgaris* L.: tsurunashiinngenn) were used for the experiments. The plants were seeded under a vermiculight. They were grown under the light intensity of 150 $\mu$mol quanta/m$^2$·s. Normal leaves derived from the plant bodies of 2 to 4 weeks old were used for the experiments.

(Method for Administration of Sample Compounds)

In the case of rice plant, a portion containing petiole was excised from the plant bodies and it was immersed into 10 ml of sample compound in a tube. It was incubated for 30 min at 25° C. under 150 $\mu$mol quanta/m$^2$·s of illumination. After administration of sample compounds, the leaves of rice were sliced and put in a chamber with diameter of 35 mm and the rate of oxygen generation ($\mu$mol O$_2$/m$^2$·s) was estimated. In the case of other plants, a leaf disk with diameter of 35 mm was prepared prior to the experiment. It was immersed into 10 ml of sample solution in a dish and the sample solution was administrated under the same condition as rice plant. After the administration, water in the leaf disk was excluded, the leaf was set in the chamber and the ability of photosynthesis was measured on the leaf. Then, the sample solution was prepared by dissolving arbitrary amount of sample compounds into 10 mM potassium phosphate buffer (pH7) and sample solution thus prepared was used for the experiments. Potassium formate, sodium formate and ammonium formate were used for the sample compounds.

(Estimation of Photosynthetic Ability in terms of Oxygen Generation Rate)

Generation of oxygen was measured by clark type oxygen electrode. The cuvette (LD2/2 type), the oxygen electrode controller (CB 1-D3 type) and the light source (LS-2, Hansatec corp.) were adopted as components of the measuring device. The chamber of cuvette contained in this device is composed of combination of a chamber, capable of hermetically sealing with diameter of 35 mm and volume of 5 ml, and an oxygen electrode. As upper side of the chamber is transparent, arbitrary intensity of light can be illuminated. The plant body described above, after administration of formic acid, was enclosed in the chamber and sealed hermetically. It was illuminated using a halogen lamp as the light source, and the rate of oxygen generation was measured under the air containing 5% of carbon dioxide. Unless specified otherwise, the measurement was performed under the light adjusted to a intensity of 253 $\mu$mol quanta/m$^2$·s using a red filter or an attenuation filter. The oxygen generation was calculated by dividing the obtained value with the surface area of the leaf.

(The Condition of Photo-oxidation Damage)

After measurement of rate of photosynthesis as described above, the air without carbon dioxide was introduced into the chamber and the light was illuminated at the intensity of 1600 $\mu$mol quanta/m$^2$·s for a certain period. The photo-oxidation damage, caused by lack of carbon dioxide, was induced under the condition described above. The rate of oxygen generation was measured after this treatment and inhibition of photosynthetic ability caused by photo-oxidation damage was thus evaluated.

(The Effect of Formate Salts on Photo-oxidation Damage)

Figure 2:
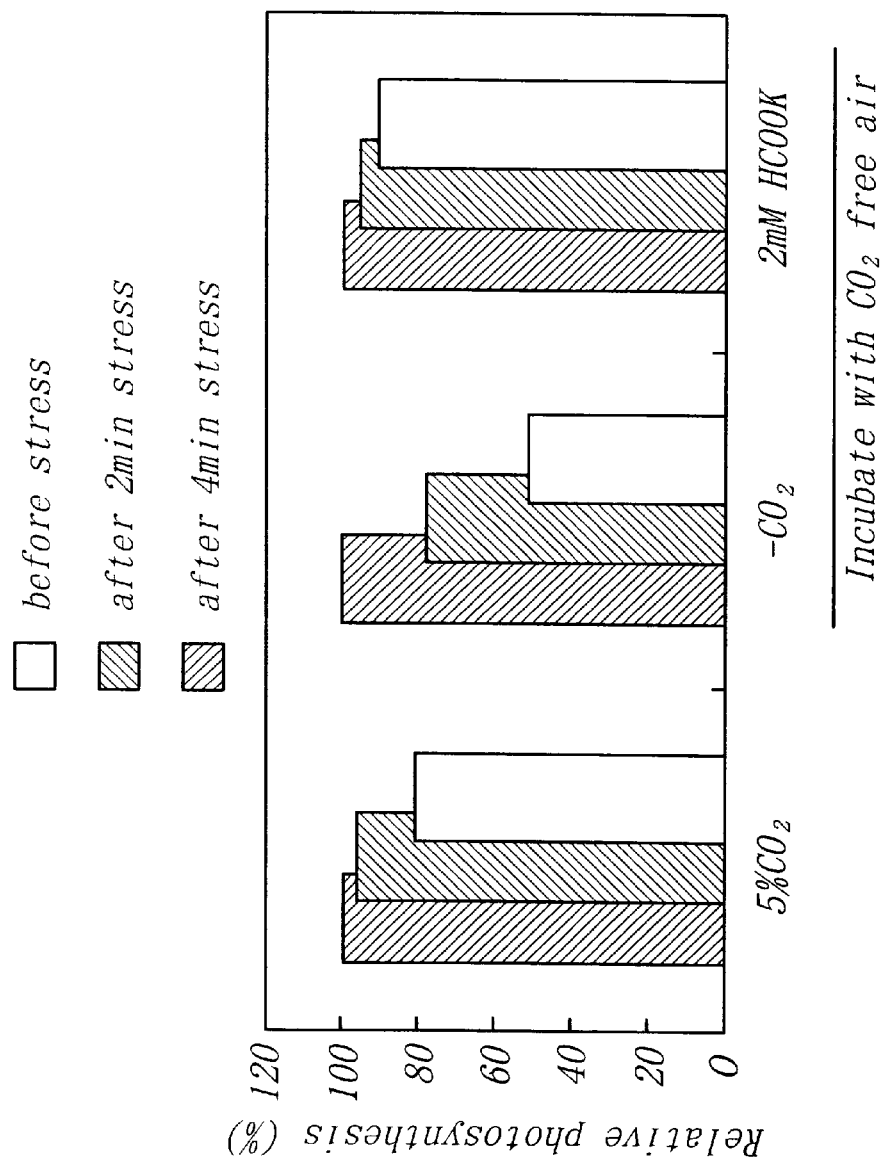
FIG. 2 is a graph showing time course of photo-oxidation damage of rice and inhibition of photo-oxidation damage by potassium formate.

The effect of various formate salts on the photo-oxidation damage of rice was investigated. The rate of oxygen generation was reduced to about 30% by 8 min of strong light illumination in the absence of carbon dioxide as shown in FIG. 1. On the other hand, plant bodies retained 90% of oxygen generation activity by addition of 2 mM of potassium formate. Such protection effect was the most prominent on potassium formate. Two mM of formate salts exhibited potency on protection of oxygen generation ability in the turn of potassium formate, sodium formate and ammonium formate. Moreover, time course of protection of photo-oxidation damage by formate salts was investigated. Prolonged treatment (2 min, 4 min) of photo-oxidation damage caused damage on photosynthetic ability in a time dependent manner as shown in FIG. 2. Despite of it, the damage on photosynthetic ability was inhibited in the presence of 2 mM potassium formate.

Figure 3:
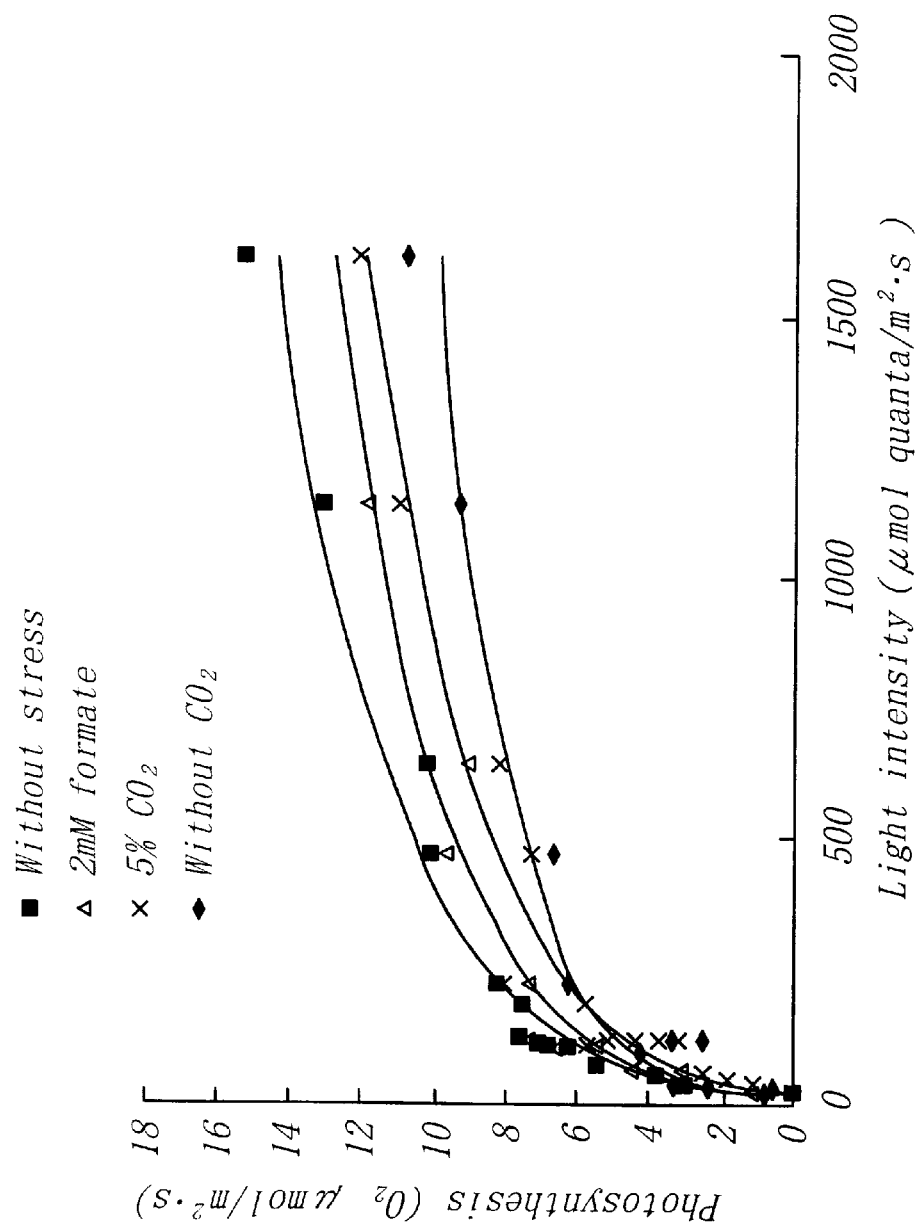
FIG. 3 is a graph showing effect of formic acid on photo-synthetic ability of rice under various intensities of illumination after photo-oxidation damage.
Figure 4:
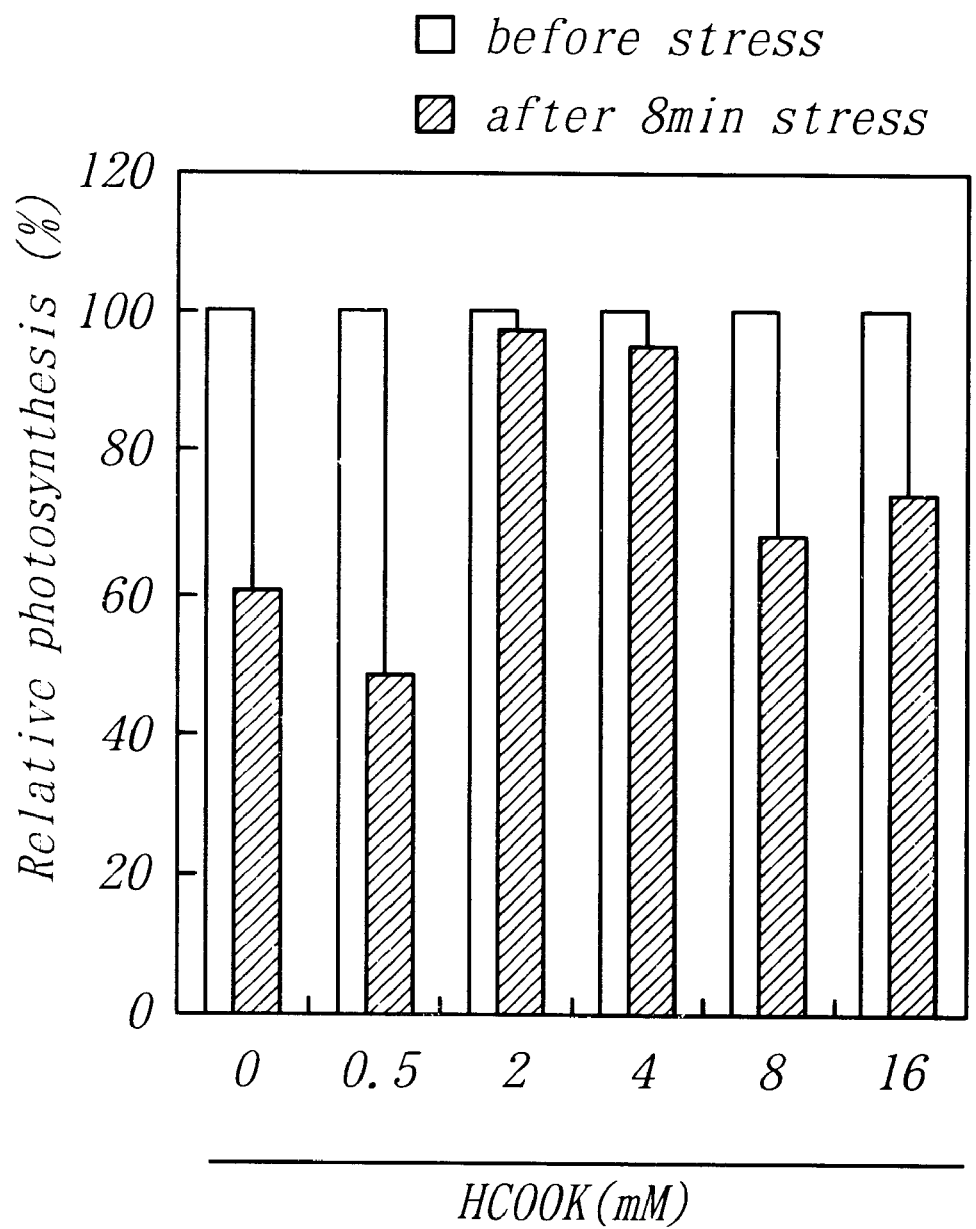
FIG. 4 is a graph showing dose-dependency of potassium formate concentration on inhibition of photo-oxidation damage of rice.

Furthermore, the effect of light intensity on photosynthetic ability of rice sample was investigated after photo-oxidation damage treatment. As shown in FIG. 3, the inclination was not altered under weak light illumination, whereas the addition of formate salt inhibited damage on photosynthetic ability under strong light illumination. From this result, enzyme system concerning calvin cycle might be protected in the presence of formate salts. Moreover, the dose-dependency of potassium formate concentration on protection of photo-oxidation damage, caused by potassium formate, was investigated on rice. As the result, 2 mM or 4 mM of potassium formate exhibited optimum protection on photo-oxidation damage as shown in FIG. 4.

Figure 5:
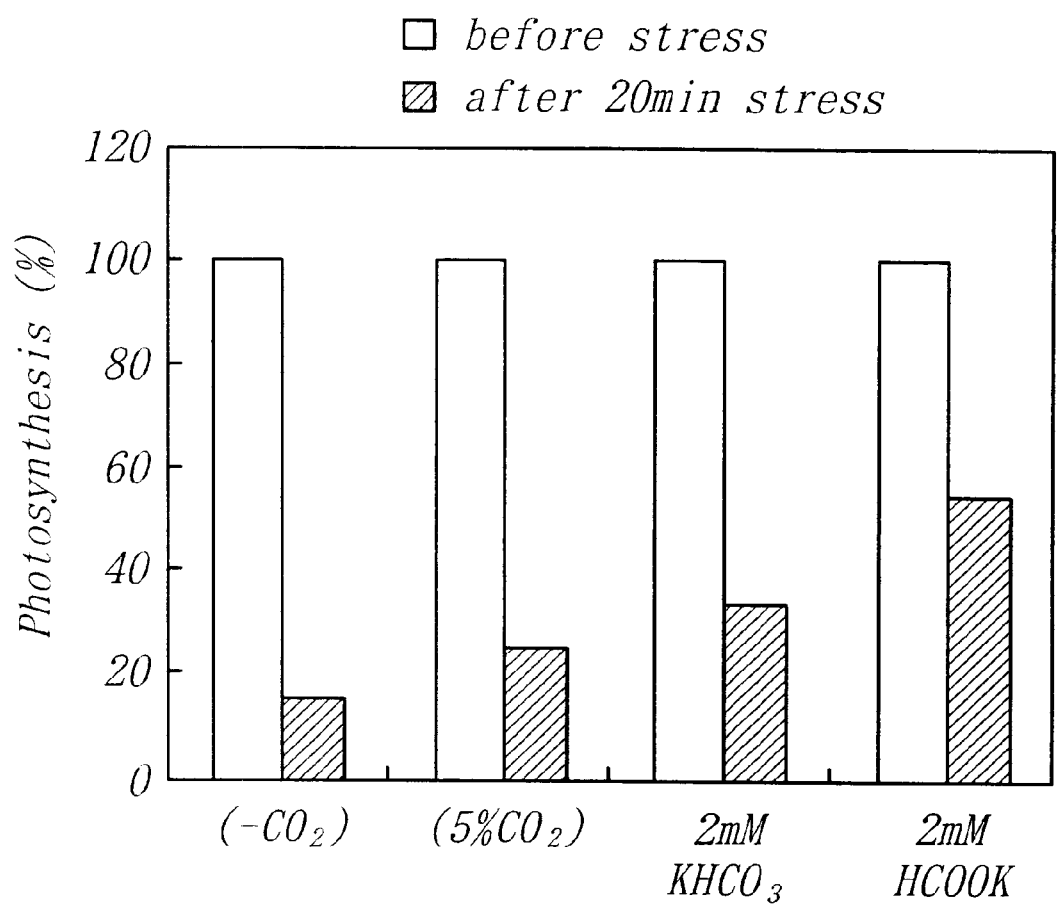
FIG. 5 is a graph showing inhibition of photo-oxidation damage of kidney bean by formate salts.
Figure 6:
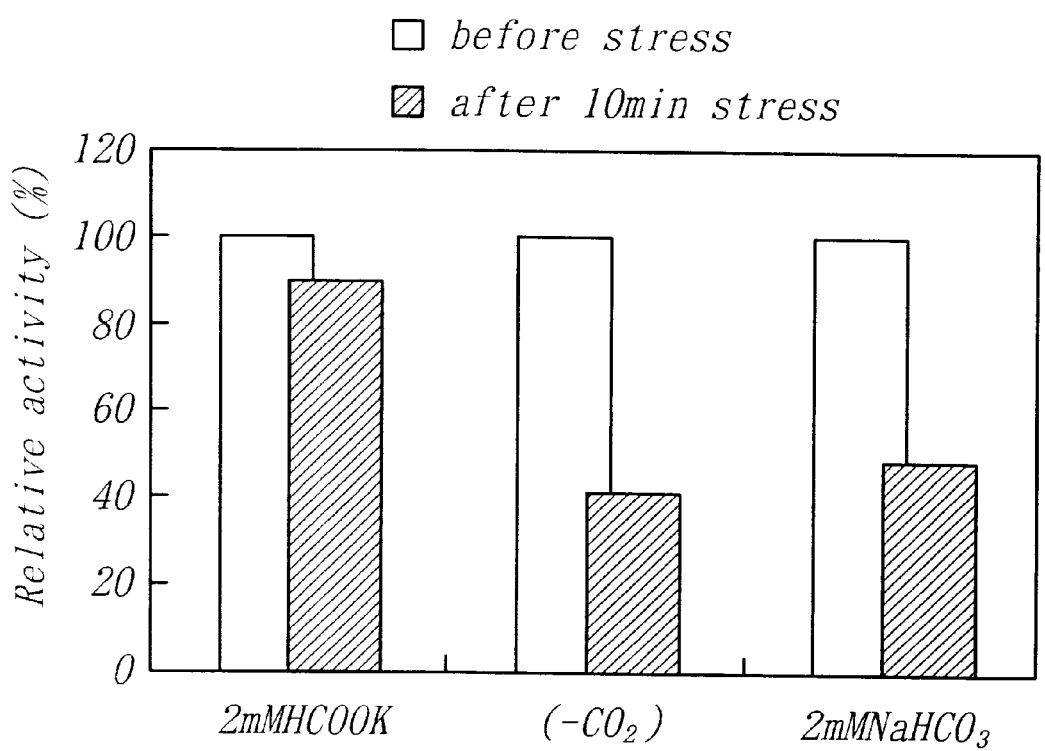
FIG. 6 is a graph showing inhibition of photo-oxidation damage of tabacco by formate salts.

The effect of formate salts on photo-oxidation damage was also observed on kidney bean and tabacco. Administration of 2 mM of potassium formate exhibited inhibition on oxygen generation rate caused by photo-oxidation damage. FIG. 5 shows the result on kidney bean and FIG. 6 shows the result on tabacco plant.

(Fluorescence Measurement of Chlorophyl)

Figure 7:
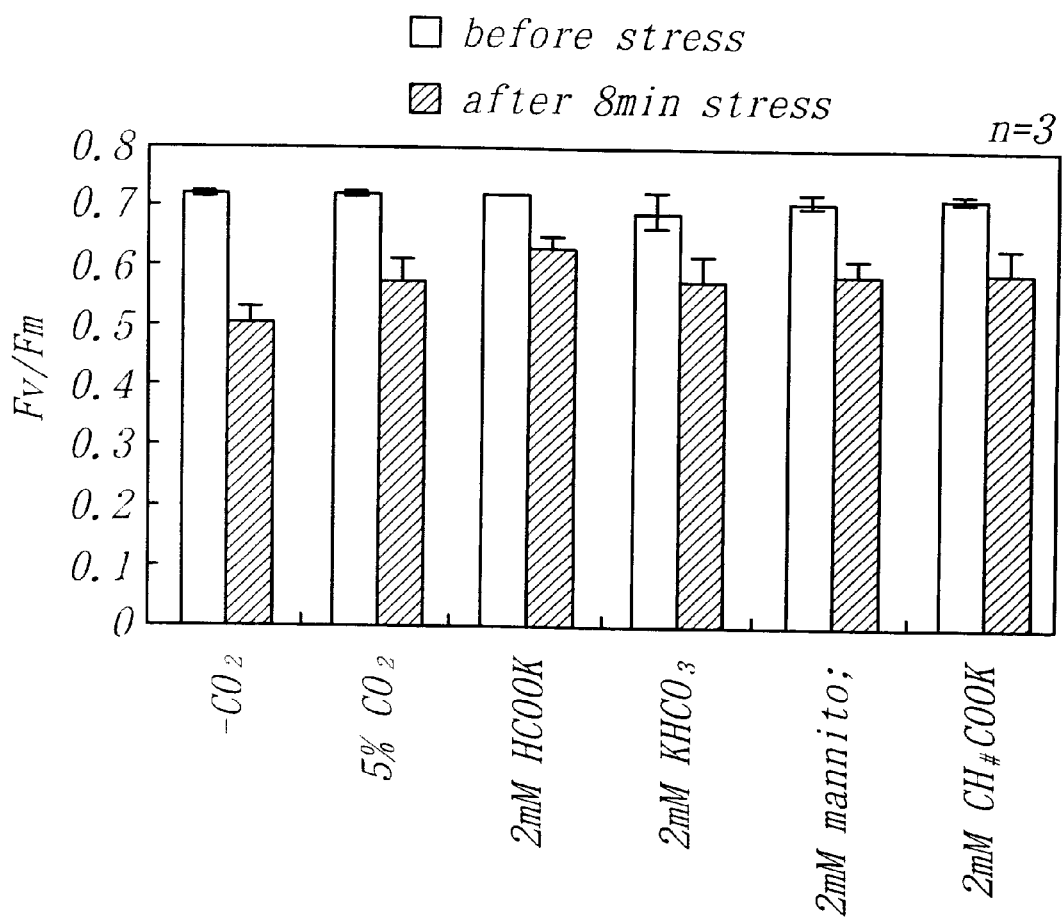
FIG. 7 is a graph showing result of fluorescence analysis of rice after photo-oxidation damage.

To estimate sanity of photo-system, the fluorescence originated from chlorophyl, the center of photo-system, was measured on rice under the same condition described above after photo-oxidation damage. The measurement was performed by chlorophyl fluorometer (PAM101 emitter and detector, PAM103: light pulse generator, WALTZ). The condition of measurement was as follows. Excitation: 100 KHz, intensity 5, saturated light: 900 ms. The fluorescence was measured before and after photo-oxidation damage to estimate Fv/Fm value. The condition of plant growth, the method to administrate formic acid and the preparation of samples adopted in this experiment were the same as the experiments on oxygen generation. The result of fluorescence measurement revealed that damage on photo-system, caused by photo-oxidation damage, was avoided by addition of 2 mM formate (FIG. 7).

(Plant Growth Test)

The effect of formate salts addition observed on plant growth was investigated. The seeds of rice were sterilized and seeded into a glass tube (130 mm×40 mm I.D) containing medium described below. The contents of the medium are ½MS salt, 0.1% gellan gum and various concentrations of sodium formate. The pH was adjusted to 6.0 by addition of 1N sodium hydroxide and the medium was sterilized by autoclave treatment. The rice seeds were grown under 25° C. for 16 hours in the light and 8 hours in the dark, under 40 $\mu$mol quanta/m$^2$.s of illumination. After cultivation for 2 weeks under this condition, the extent of growth was estimated by measurement of length of the aerial part and wet weight of plant bodies.

Figure 8:
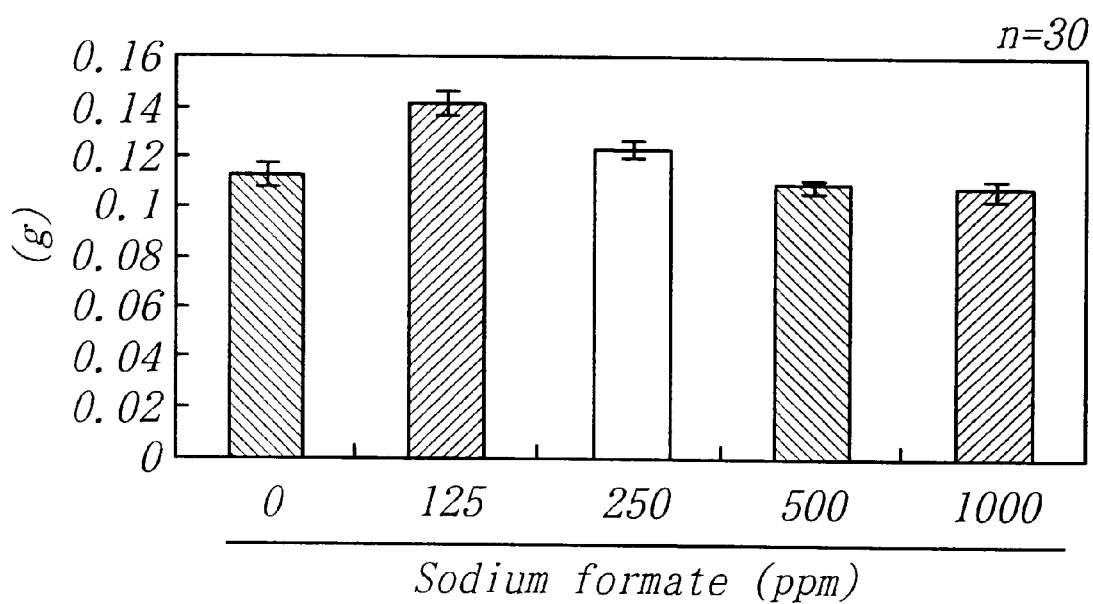
FIG. 8 is a graph showing dose dependency of sodium formate concentration on wet weight of rice plant bodies.
Figure 9:
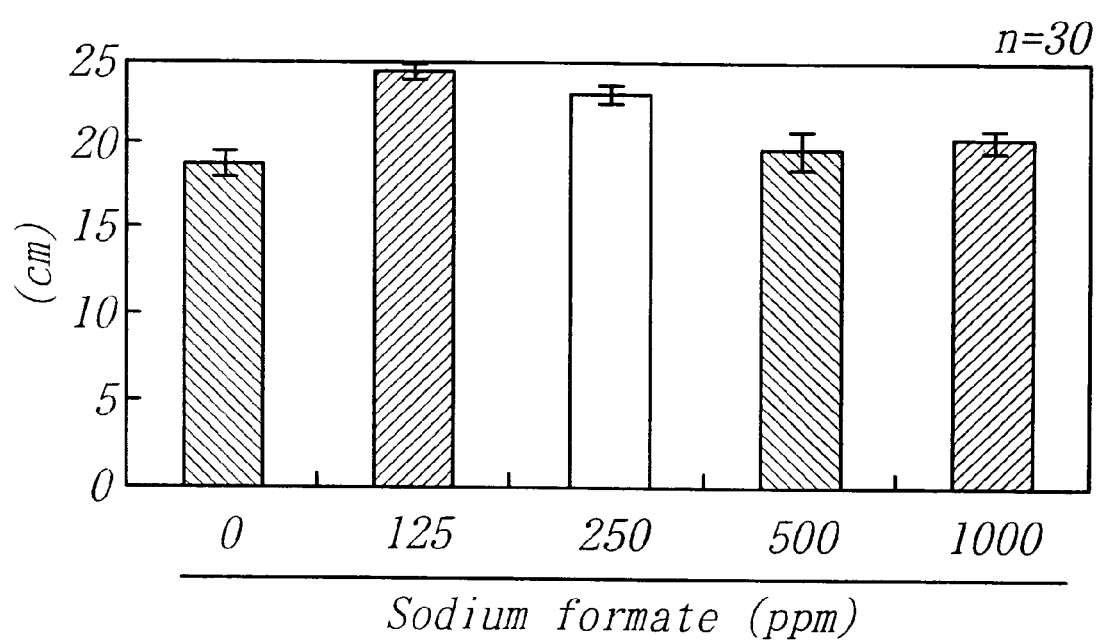
FIG. 9 is a graph showing dose dependency of sodium formate concentration on height of aerial part of rice plant bodies.

The effect of formate salts on growth of rice plant bodies, measured as described above, was investigated. The effect of sodium formate was investigated under various concentrations to reveal that, addition of 125 ppm of sodium formate resulted in 25% of growth promotion, both on wet weight of plant bodies (FIG. 8) and length of aerial part (FIG. 9). The growth promotion effect disappeared at the presence of 1000 ppm of sodium formate. The student t-test was performed on difference of average value calculated on 30 samples. The result showed significant difference at a significantly low level of less than 1%. Therefore, the formulation containing 125 ppm of sodium formate with pH adjusted to pH 7 is effective for promotion of plant growth. Formic acid, the effective ingredient of this formulation, can be added to ordinal phosphate fertilizer or nitrogen fertilizer. As an example of such fertilizer, a commercial fertilizer "hyponex" is preferred.

(Uptake of Formic Acid into Plant Bodies)

Figure 10:
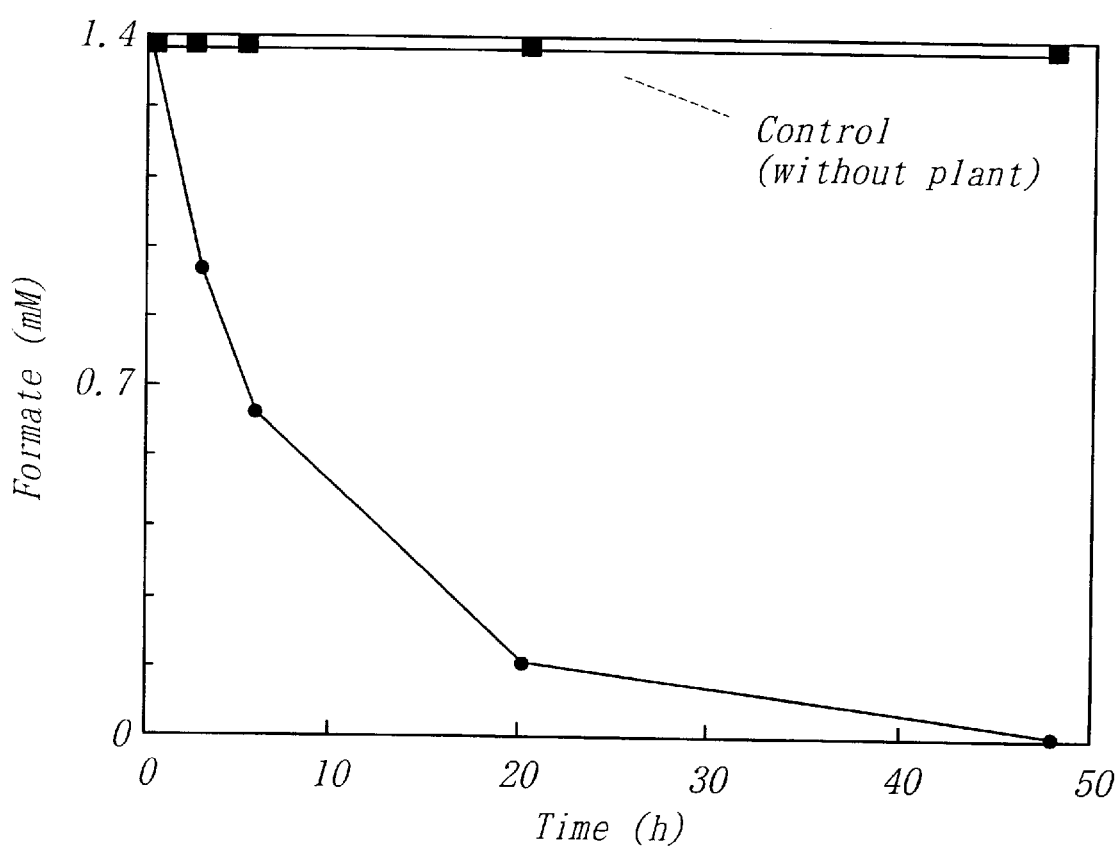
FIG. 10 is a graph showing time course of formic acid uptake measured on rice.

To confirm metabolism of formic acid, uptake of formic acid into plant body was investigated under the condition described at "plant growth test", using rice cultivated for 2 weeks at 25° C. Five plant bodies were harvested and washed by water, then 2.5 ml of 1.4 mM sodium formate was added and incubated under illuminated condition (40 $\mu$mol quanta/m$^2$.s) at 25° C. Twenty-five $\mu$l of the solution was sampled at each period and formic acid concentration in the solution was determined by absorbance. The result exhibited rapid uptake of formic acid and formic acid was not detected in the solution after 48 hours. FIG. 10 shows the result as the average value of three independent experiments. Formic acid is assumed to be absorbed in the plant body because decrease of formic acid was not observed without the plant body (control).

(Formation of Carbon Dioxide by Administration of Formic Acid)

Figure 11:
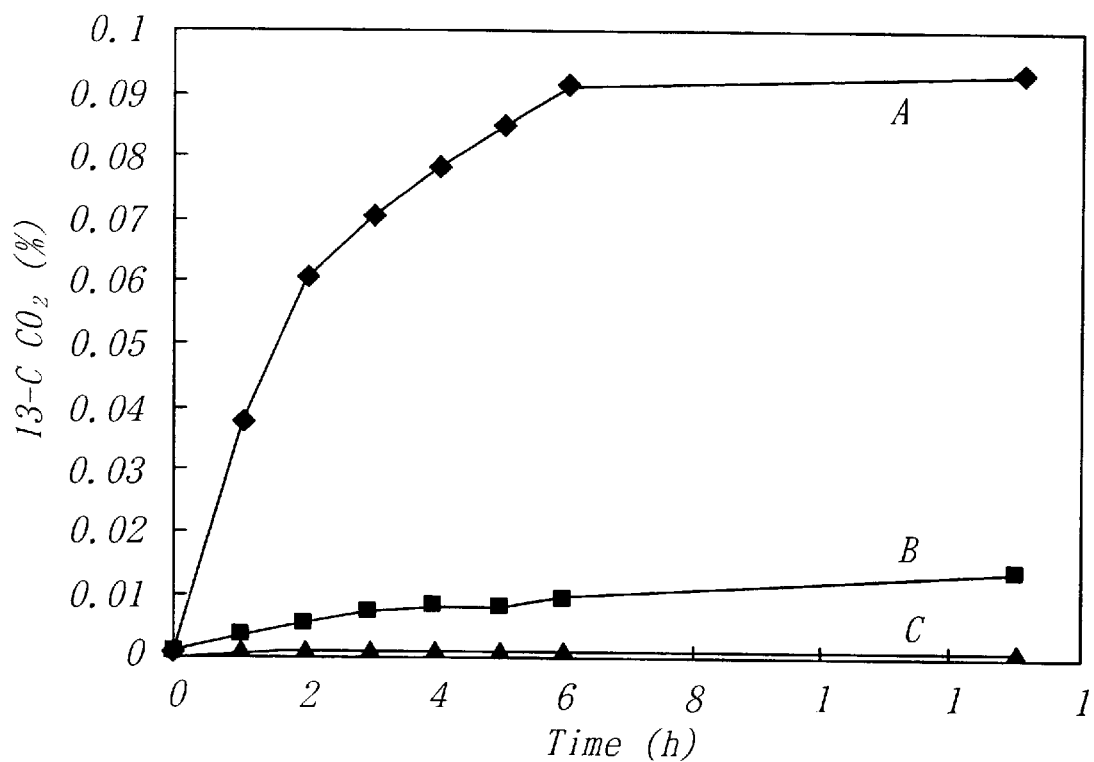
FIG. 11 is a graph showing time course of carbon dioxide formation originated from formic acid measured on rice.

The extent of carbon dioxide produced by metabolism of formic acid was measured using rice plant bodies cultivated at 25° C. for two weeks as described above. The glass container containing 5 ml of 1.4 mM [$^{12}$C] or [$^{13}$C] sodium formate (pH7) was sealed by gumseptam and incubated at 25° C. under dark condition. Twenty-five $\mu$l of the solution was sampled at each period and content of carbon dioxide in the supernatant was analyzed by gas chromatography-mass spectrometry (GC-MS). As the result, 9% (FIG. 11A) or 1% (FIG. 11B) of [$^{13}$C] $CO_2$, compared to total carbon dioxide, was detected in samples with addition of [$^{12}$C] or [$^{13}$C] formic acid, respectively, as shown in FIG. 11. As natural content of [$^{13}$C] is about 1%, increased [$^{13}$C] $CO_2$ would be originated from added formic acid. This result indicates existence of certain mechanism that converts formic acid to carbon dioxide in rice, for example, formate dehydrogenase (FDH).

(Measurement of FDH Activity)

Figure 12:
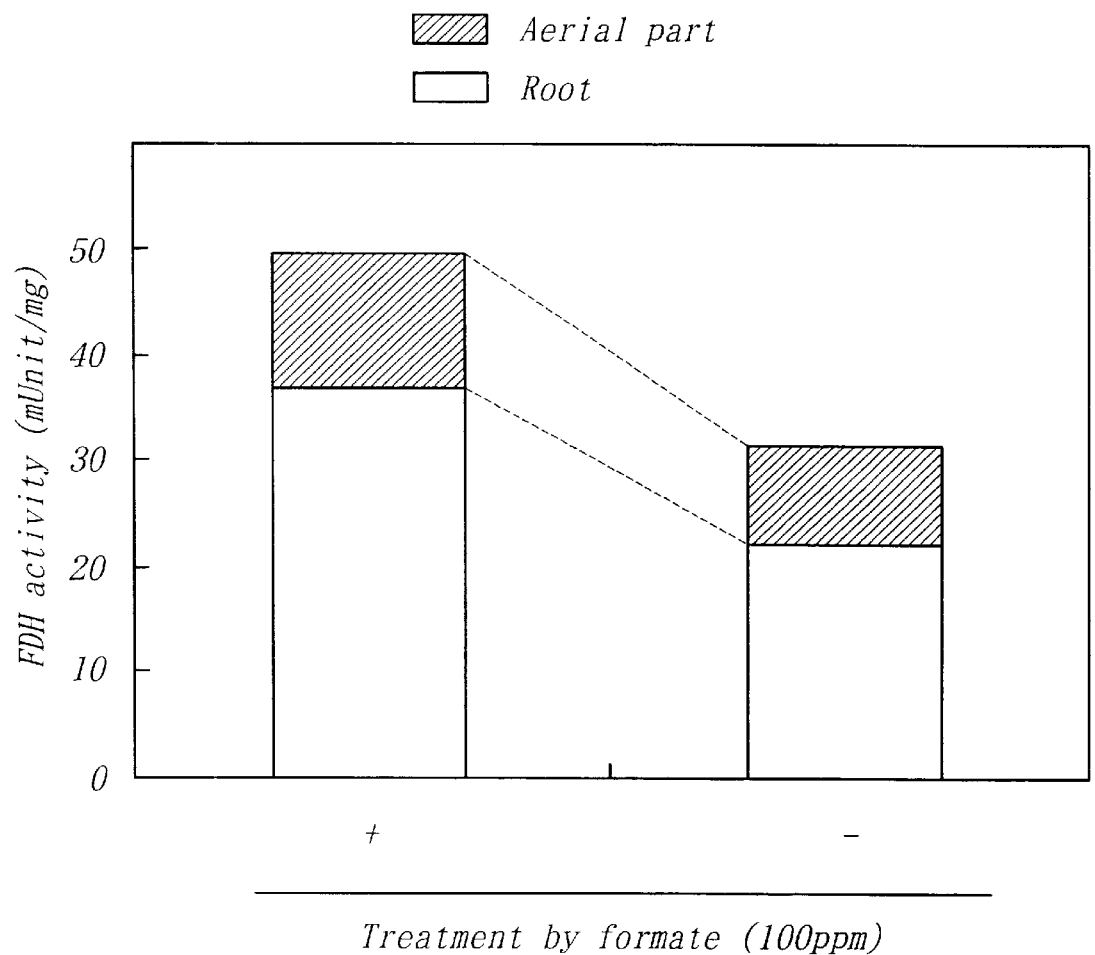
FIG. 12 is a graph showing activity of formate dehydrogenase measured on aerial part and ground part of rice. plant bodies.

Then the alteration of FDH activity by administration of formic acid was investigated. The rice plant bodies were cultivated in the presence or absence of 1.4 mM formic acid at 25° C. for two weeks. The aerial part and the ground part (root) was separated and the crude enzyme solution was prepared from each part. The enzyme solution was prepared to 1.5 mg/ml and FDH activities of the samples were measured. The FDH activity was measured using [$^{13}$C] formic acid as the substrate and detecting [$^{13}$C] $CO_2$ in the supernatant by GC-MS. When the root of rice was cultivated in the presence of formic acid, its activity was about twice compared to that of control group (without addition of formic acid), indicating increase of enzyme activity (FIG. 12).

(Isolation of RNA)

Isolation of total RNA was performed as described below. In the case of utilization for northern analysis, total RNA was isolated from leaf and root of rice cultivated under condition described above, using Isogen RNA purification kit (Nippon gene). In the case of cDNA preparation, total RNA was isolated using Plant RNA kit (QIAGEN). After treatment by DNAase, oligo(dT)12-18 primer (GIBCOBRL) was used for reverse-transcription and cDNA was prepared.

(Cloning of cDNA Encoding FDH)

From sequence homology with FDH derived from potato, three clones of rice cDNA were selected from DDBJ (DDBJ accession nos. D23989, D23770 and D48722). The alignment of these cDNA clones revealed that, these cDNA sequences are constituting partial sequence of FDH homolog consisted of 970 bp. Then this partial sequence was cloned from rice cDNA using PCR. Using this sequence, full length of FDH gene was isolated using 3'- and 5'-Full Race core Set (Takara biochemicals).

(Determination and Analysis of the Base Sequence)

PCR products were subcloned to PCR2.1 (Invitrogen) or pUC18 (Takara biochemicals). The sequence of subcloned product was sequenced by DNA sequencer (ABI 310, Applied Biosystems), using M13 primer and sequencing kit (dye terminator cycle sequencing ready reaction kit, Perkin Elmer). The result showed that, the gene consists of a base sequence with reading frame of 1450 base pair (sequence list: sequence number 2). The sequence was analyzed using genetic-mac (genetic information processing software), a sequence analysis software. The result revealed that the deduced amino acid sequence of FDH consists of 376 base pair (sequence list: sequence number 1), with calculated molecular weight of 41.2kDa and isoelectric point of 7.39. The sequence homology was compared between this sequence and FDH sequences originated from other known plants. The result exhibited high homology with known FDH sequences of other plants. That is, the amino acid sequence of rice (*C.sativa*) FDH exhibited high homology with potato (*S.tuberosum*: 82.7%) FDH and barley (*H.vulgare* : 91.7%) FDH. Moreover, the formic acid binding site (282) and the NAD binding site (189-223) were shown to be highly conserved among these plants (FIG. 13). As amino acid sequence of rice FDH and base sequence encoding the enzyme were determined, resistance against photo-oxidation damage might be rendered to a plant by incorporation of the gene described in sequence number 2 in the sequence list.

(Expression of cDNA in *E.coli*.)

The amino acid sequence deduced from the gene obtained by the cloning described above showed high homology with known FDH. Therefore, this sequence was expected to encodes FDH and the cDNA was expressed in *E.coli* to confirm the function of this sequence. The plasmid, utilised to be expressed in *E.coli*, was prepared by insertion of target fragment into pUC18 plasmid abscission. The fragment was prepared by PCR amplification using primers containing restriction enzyme recognition sites and then the product was treated by restriction enzyme. The fragment thus prepared was inserted into pUC18 plasmid. The primer containing EcoRI site and BamHI site was prepared in two series and the insertion fragments were prepared for two orientations. That is, insertion orientations of the sequence are sense orientation and anti-sense orientation. The primers used were 5'-cggaattcatggcgatgtggagggcggc-3'(forward direction) and 5'-cgggatccttactggtactggc-3'(reverse direction) for the sense orientation and 5'-cgggatccatggcgatgtggagggcg-3'(forward direction) and 5'-cggaattcttactggtactggctcgcgagc-3'(reverse direction) for the anti-sense orientation (Reverse). The PCR products using the primers were incorporated into pUC18 plasmid by EcoRI site and the BamHI site, to the initiation codon or the termination codon. The insertion of cloned sequence was confirmed by sequencing using di-deoxy method utilizing M13 primer.

The *E.coli* JM109 strain was transformed by the plasmid thus prepared. Transformed *E.coli* was cultured in 50 ml of LB medium (containing 50 mg/ml ampicillin) until the absorbance at 660 nm reached to 3.0. It was cultured under aerobic condition at temperature of 20° C., which is a lower temperature compared to ordinary condition. Then expression of protein was induced by 0.2 mM IPTG at 20 ° C. for 6 hours.

The bacteria was collected, then washed by water and re-suspended into 2 ml of solution containing 10 mM SPB (pH 7.0), 100 mM NaCl, 0.5% triton X-100 and 2 mM DTT. The bacteria obtained was disrupted by sonication and the crude enzyme solution was prepared from supernatant of the centrifugation. The centrifugation was performed at 15,000 g for 15 min and the supernatant was obtained to measure enzyme activity. The intrinsic FDH of E.coli does not utilize NADH as a co-enzyme, as described in the report, the protein did not exhibit enzyme activity at the actual measurement. It was also revealed that, only the fragments with sense-orientated insertion exhibited enzyme activity. Therefore, it was strongly suggested that the sequence would be FDH protein with dependency to NAD.

(Alteration of FDH Gene Expression by Administration of Formic Acid)

Figure 14:
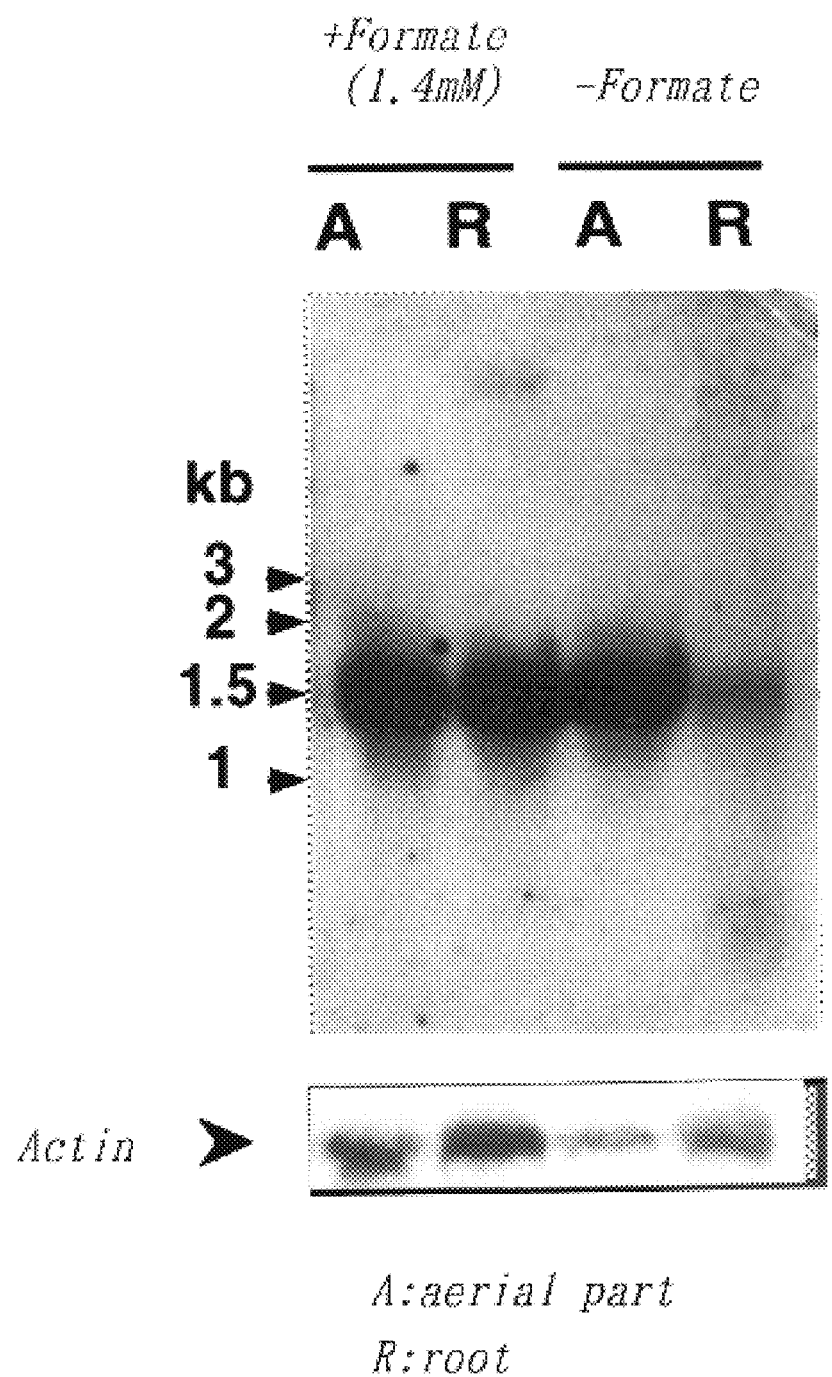
FIG. 14 is a photograph of northern blotting, indicating alteration of FDH gene expression by administration of formic acid.

The enzyme activity of rice FDH increased by administration of formic acid. Therefore, the expression of FDH gene, isolated in this experiment, was analyzed. Like measurement of enzyme activity, the rice plant was cultivated with or without formic acid. RNA was prepared from the aerial part and the ground part (root) respectively and the northern analysis was performed on these samples. Forty μg of the total RNA was applied to each lane and electrophoresis was performed on 1% agarose gel (containing 2.2 M formaldehyde). The gel was charged for the capillary blotting using Hybond N+membrane (Amersham) using 20×SSC. The hybridization was performed according to instruction of AlkPhosDIREST (Amersham) and detection was performed using CDP-Star (Amersham). The FDH cDNA (open reading frame:1130 bp), amplified by PCR, was used as probe DNA. The expression of FDH gene, measured on ground part of rice, exhibited significant increase by pretreatment with formic acid administration (FIG. 14).

As described above, a metabolite pathway described below exists in some plant species including rice. That is, methanol is metabolized to carbon dioxide by oxidation in a stepwise manner, through conversion to formaldehyde and formic acid as the intermediates. Then methanol, an alcohol with a low molecular weight, might be effective for inhibition of photo-oxidation damage and investigation was performed on the hypothesis. The plant bodies used in the experiment, the method to administrate sample substance, evaluation of photosynthesis by measurement of oxygen generation rate, photo-oxidation damage measurement and chlorophyl fluorescent measurement were performed as described in the experiments of formic acid.

(Effect of Methanol on Photosynthetic Ability of Rice)

Figure 15:
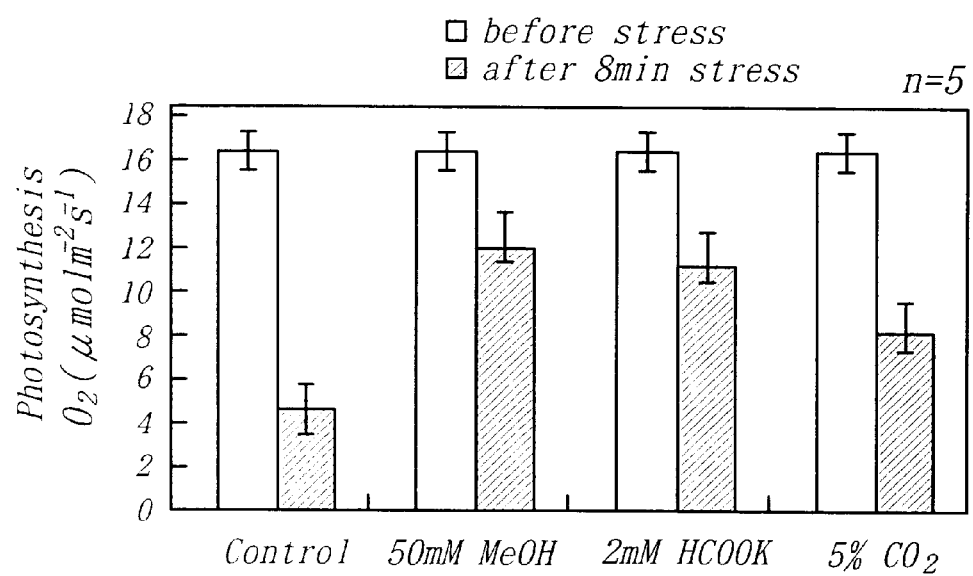
FIG. 15 is a graph showing effect of methanol and potassium formate on photo-oxidation damage of rice.
Figure 16:
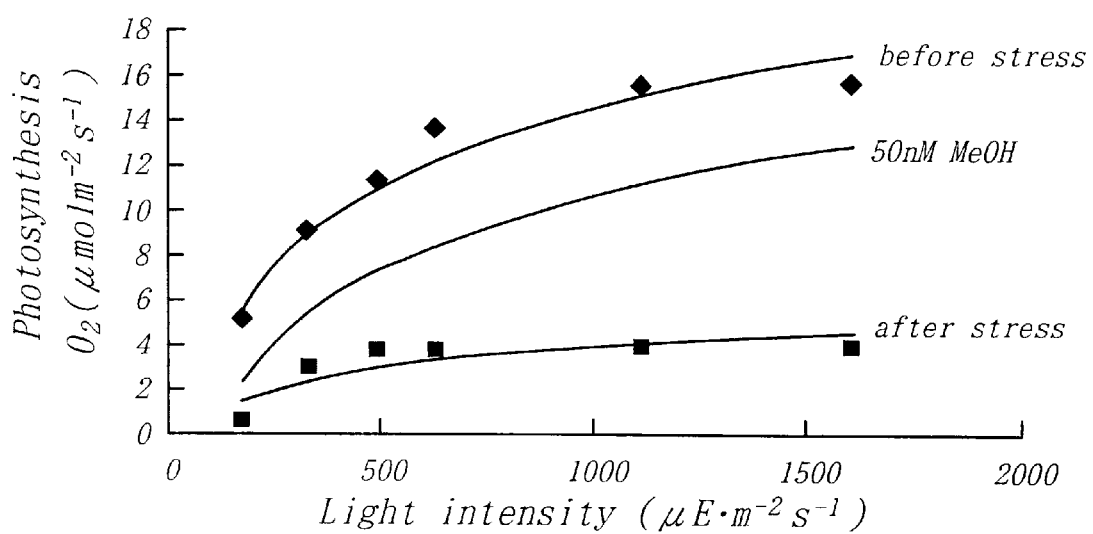
FIG. 16 is a graph showing effect of methanol on photo-synthetic ability of rice under various intensities of light illumination.

By analysis of oxygen generation rate, effect of methanol on photosynthetic ability was investigated. The result indicated that, when oxygen generation rate of the control sample was reduced to 30%, the residual photosynthetic ability was 70% and 60% by addition of methanol and formate salt, respectively (FIG. 15). The dependency of light intensity was investigated after photo-oxidation damage of rice, using oxygen generation rate as an indicator (FIG. 16). The administration of methanol avoided photo-oxidation damage as shown in FIG. 16, especially under strong light illumination.

(Effect of Methanol on Chlorophyl Fluorescence Analysis of Rice Plant)

Figure 17:
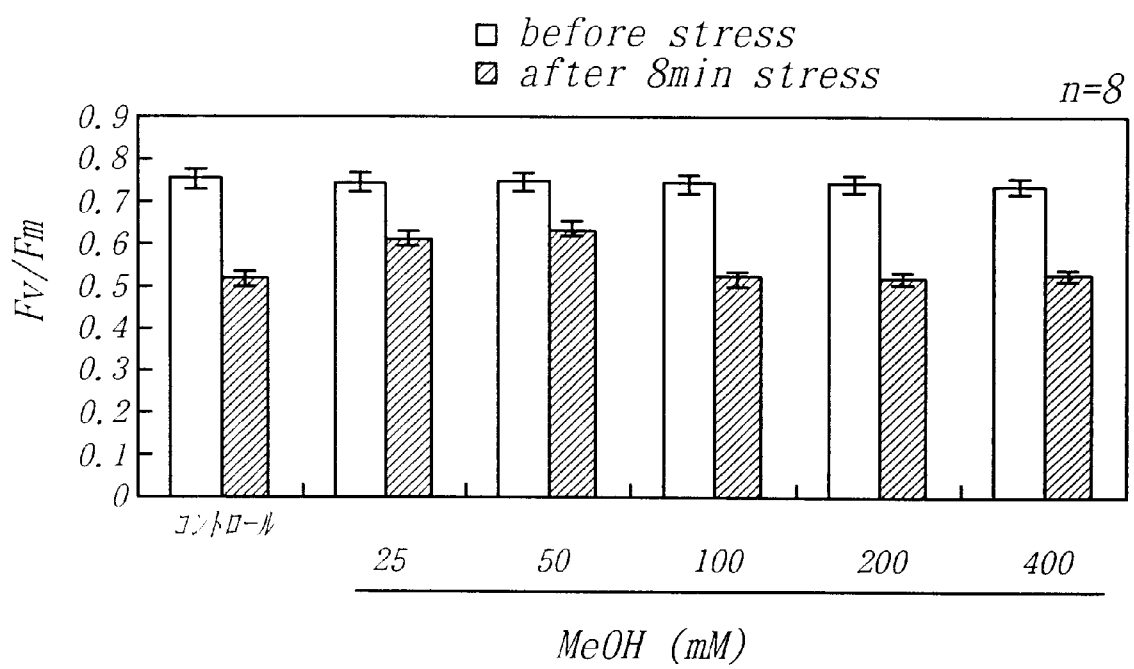
FIG. 17 is a graph showing dose-dependency of methanol on inhibition of photo-oxidation damage of rice measured by fluorescence analysis.

Furthermore, chlorophyl fluorescence analysis was performed under presence of various concentrations of methanol using rice. The addition of 25 mM or 50 mM methanol resulted in significant inhibition of reduction of Fv/Fm value caused by photo-oxidation damage (FIG. 17).

(Effect of Methanol on Chlorophyl Fluorescence Analysis of Tabacco and Kidney Bean)

Figure 18:
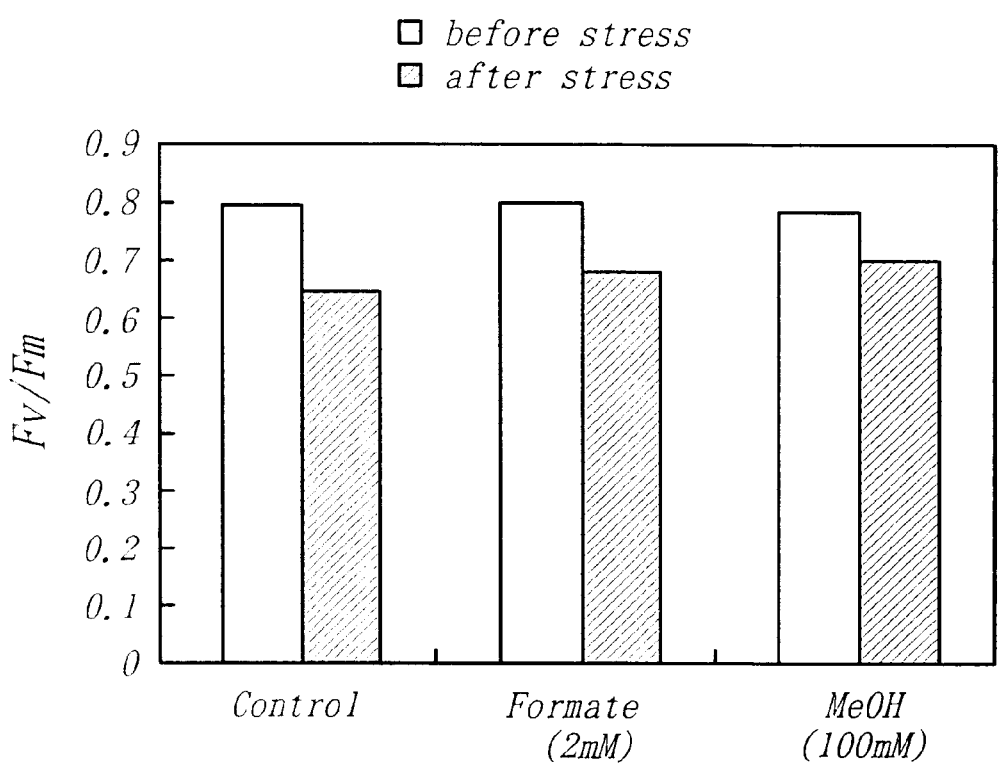
FIG. 18 is a graph showing effect of methanol and formic acid on tabacco, measured by fluorescence analysis.
Figure 19:
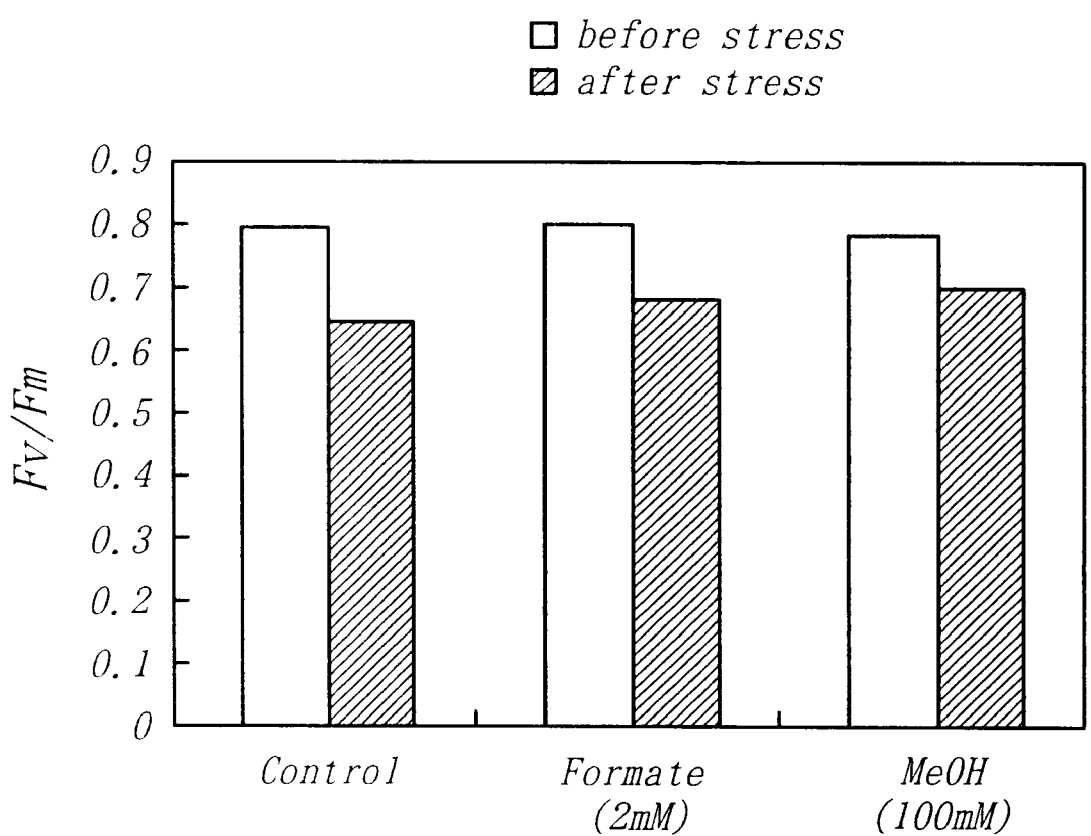
FIG. 19 is a graph showing effect of methanol and formic acid on kidney bean, measured by fluorescence analysis.

Furthermore, the effect of methanol addition was also investigated on tabacco (FIG. 18) and kidney bean (FIG. 19). The chlorophyl fluorescence analysis revealed potency of 100 mM methanol addition, as the same as 2 mM formic acid addition. Then the damage on photo-system, caused by photo-oxidation damage, was significantly alleviated by addition of methanol.

A method to promote plant growth was proposed by this invention. It was achieved by administration of formic acid, an organic acid of low molecular weight, through avoidance of photo-oxidation damage. Moreover, amino acid sequence of formate dehydrogenase and base sequence encoding the enzyme were also proposed. In addition, a method to promote plant growth by administration of methanol, through avoidance of photooxidation damage, was proposed.

Sequence list
<110>Applicant name: President of Nara Institute of Science and Technology
<120>Title of invention: A method to promote growth of a plant
<150>Ealier patent application: JP 11-56776, JP 2000-36153
<151>Ealier application filing date: 1999-3-4, 2000-2-15
<160>Number of SEQ ID Nos: 2
<210>SEQ ID No: 1
<211>Length: 376
<212>Type: PRT
<213>Organism: Rice formate dehydrogenase
<400>Sequence:

| MAMWRAAAGH LLGRALGSRA AHTSAGSKKI VGVFYKGGEY ADKNPNFVGC VEGALGIREW | 60 |
| LESKGHHYIV TDDKEGLNSE LEKHIEDMHV LITTPFHPAY VSAERIKKAK NLELLLTAGI | 120 |
| GSDHIDLPAA AAAGLTVAEV TGSNTVSVAE DELMRILILL RNFLPGYQQV VHGEWNVAGI | 180 |
| AYRAYDLEGK TVGTVGAGRI GRLLLQRLKP FNCNLLYHDR LKIDPELEKE IGAKYEEDLD | 240 |
| AMLPKCDVIV INTPLTEKTR GMFNKERIAK MKKGVIIVNN ARGAIMXTQA VADACSSGOV | 300 |
| AGYGGDVWFP OPAPKGPPWR YMPNHAMTPH ISGTTIDAOL RYAAGVKDML DRYFKGEDFP | 360 |
| VQNYIVKEGQ LASQYQ | 376 |

<210>SEQ ID NO: 2
<211>Length: 1450
<212>Type: DNA
<21 3>Organism: Rice formate dehydrogenase
<400>Sequence

| cgagtcggct gcaclgatcg attccatcac tctctctctc tcgcctgctc gcggttgctg | 60 |

-continued

| | |
|---|---|
| tgcgttcgtc tcgcgatttc tcctcctcct cctgggatca tggcgatgtg gagggcggcg | 120 |
| gcggggcatc ttctcggccg cgcgctcggc tccagggccg cgcacacatc agcaggcagc | 180 |
| aagaagatcg tgggtgtgti ctacaagggc ggcgagtacg ccgacaagaa tcccaacttc | 240 |
| gtcggctgcg tggagggcgc tctcggcatc cgcgaatggc ttgagtccaa ggggcatcac | 300 |
| tacattgtca ccgacgacaa ggaggggcta aacagcgagc tggagaagca cattgaggat | 360 |
| atgcatgtct tgatcaccac cccttttccac ccagcctatg ttagcgcaga aaggatcaag | 420 |
| aaggcaaaga acctcgagct gcttctcaca gctgggattg ggtcagatca tattgatctg | 480 |
| ccagcagctg ctgcagcagg tttaactgtg gcagaggtta ccggaagtaa cactgtgtcg | 540 |
| gtggcagaag atgagctcat gcgcattttg attttgctca ggaacttctt gcccgggtat | 600 |
| cagcaggttg ttcatggtga atggaatgtt gctggcattg cctatagggc ttatgatctt | 660 |
| gaaggaaaaa ctgtggggac tgttgggget ggtcgtattg gcaggctctt acttcagcgt | 720 |
| cttaagcct ttaactgcaa cctgctgtac catgacagac ttaaaattga cccagaactt | 780 |
| gagaaagaaa ttggggccaa atatgaagag gatctcgatg ctatgcttcc aaagtgtgat | 840 |
| gtcattgtga tcaatacacc tcttacagag aaaacaagag gtatgtttaa taaagaaaga | 900 |
| attgcaaaga tgaagaaagg tgtaatcatt gtgaataatg ctcgaggagc aatcatggnt | 960 |
| acccaggcgg ttgcagacgc ttgctctagt ggtcaagttg caggctatgg tggtgatgtc | 1020 |
| tggttccccc aaccagcacc aaagggtcca ccctggcggt acatgcctaa tcatgccatg | 1080 |
| accctcata tctctgggac tacaattgat gcacagctga gatacgcagc aggagttaag | 1140 |
| gacatgctgg acaggtactt caaaggggaa gacttcccgg tgcagaacta catcgtcaag | 1200 |
| gaaggtcagc tcgcgagcca gtaccagtaa taacccttcc ttgtgtgttg ggtgtccatc | 1260 |
| ctgtggccac cttcccgcag ttaaggggaa cagagnttcg ggtagggacc aaaacaactt | 1320 |
| gtgttgttgt tgttgcctga gtgttccctg agaaactatt ggacaccgga aataatggat | 1380 |
| gcctgccatg gcaaccatgg ctccgaagaa taaaaagccc tcggattaaa cagtacaaaa | 1440 |
| aaaaaaaaa | 1450 |

What is claimed is:

1. A method to prevent photo-oxidation damage to a plant, the method comprising administration of methanol, at a concentration of not more than 100 mM, to the plant to prevent photo-oxidation damage to the plant.

2. The method according to claim 1, wherein said concentration of methanol is 50 mM.

* * * * *

UNITED STATES PATENT AND TRADEMARK OFFICE
CERTIFICATE OF CORRECTION

PATENT NO.    : 6,465,396 B1
DATED         : October 15, 2002
INVENTOR(S)   : Kobayashi et al.

It is certified that error appears in the above-identified patent and that said Letters Patent is hereby corrected as shown below:

<u>Title page,</u>
Item [30], Foreign Application Priority Data, please insert -- Japan Patent Application No. 200-036153 February 15, 2000 --.

<u>Drawings,</u>
Figure 16, "50nM MeOH" should be changed to -- 50mM MeOH --.

Signed and Sealed this

Eleventh Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,465,396 B1
DATED : October 15, 2002
INVENTOR(S) : Akio Kobayashi et al.

It is certified that error appears in the above-identified patent and that said Letters Patent is hereby corrected as shown below:

<u>Title page,</u>
Item [30], Foreign Application Priority Data, please change:
"Japan Patent Application No. 200-036153" to -- Japan Patent Application No. 2000-036153 --.

Signed and Sealed this

First Day of June, 2004

JON W. DUDAS
*Acting Director of the United States Patent and Trademark Office*